US010023525B2

(12) United States Patent
Svadberg et al.

(10) Patent No.: US 10,023,525 B2
(45) Date of Patent: Jul. 17, 2018

(54) PREPARATION OF 18F-FLUCICLOVINE

(71) Applicant: GE Healthcare Limited, Buckinghamshire (GB)

(72) Inventors: Anders Svadberg, Oslo (NO); Olav Ryan, Oslo (NO); Roger Smeets, Oslo (NO)

(73) Assignee: GE Healthcare Limited (GB)

( * ) Notice: Subject to any disclaimer, the term of this patent is extended or adjusted under 35 U.S.C. 154(b) by 135 days.

(21) Appl. No.: 15/173,839

(22) Filed: Jun. 6, 2016

(65) Prior Publication Data
US 2016/0355460 A1 Dec. 8, 2016

Related U.S. Application Data

(62) Division of application No. 14/420,493, filed as application No. PCT/EP2013/066570 on Aug. 7, 2013, now Pat. No. 9,359,288.

(30) Foreign Application Priority Data

Aug. 9, 2012 (GB) .................................. 1214220.4

(51) Int. Cl.
B01J 16/00 (2006.01)
B01J 19/00 (2006.01)
B01J 19/24 (2006.01)
G21G 1/00 (2006.01)
C07B 59/00 (2006.01)
C07C 227/16 (2006.01)
C07C 227/18 (2006.01)
C07C 227/20 (2006.01)
C07C 227/40 (2006.01)
C07C 269/06 (2006.01)
G21G 1/10 (2006.01)
C07C 227/00 (2006.01)
C07C 227/14 (2006.01)
C07C 227/38 (2006.01)
C07C 269/00 (2006.01)
C07C 271/06 (2006.01)
C07C 271/08 (2006.01)
C07C 271/24 (2006.01)

(52) U.S. Cl.
CPC ............. C07C 227/16 (2013.01); B01J 16/00 (2013.01); B01J 19/24 (2013.01); B01J 19/245 (2013.01); B01J 19/248 (2013.01); C07B 59/001 (2013.01); C07C 227/18 (2013.01); C07C 227/20 (2013.01); C07C 227/40 (2013.01); C07C 269/06 (2013.01); G21G 1/10 (2013.01); B01J 2219/24 (2013.01); B01J 2219/2401 (2013.01); C07B 2200/05 (2013.01); C07B 2200/09 (2013.01); C07C 2101/04 (2013.01); C07C 2601/04 (2017.05)

(58) Field of Classification Search
CPC ... B01J 16/00; B01J 19/00; B01J 19/24; B01J 19/245; B01J 19/248; B01J 2219/24; B01J 2219/2401; C07B 59/00; C07B 59/001; C07B 2203/00; C07B 2203/05; C07B 2203/09; C07C 227/00; C07C 227/16; C07C 227/18; C07C 227/20; C07C 227/38; C07C 227/40; C07C 269/00; C07C 269/06; C07C 271/00; C07C 271/06; C07C 271/08; C07C 271/24; C07C 227/14; G21G 1/00; G21G 1/001; G21G 1/0015
See application file for complete search history.

(56) References Cited

U.S. PATENT DOCUMENTS

| 5,808,146 A | 9/1998 | Goodman et al. |
|---|---|---|
| 7,897,811 B2 | 3/2011 | Hayashi et al. |
| 8,269,035 B2 | 9/2012 | Kurosaki et al. |
| 8,343,459 B2 | 1/2013 | Nakamura et al. |
| 8,563,771 B2 | 10/2013 | Toyama et al. |
| 8,969,580 B2 | 3/2015 | Horn et al. |
| 9,061,977 B2 | 6/2015 | Nilsen et al. |
| 9,238,596 B2 | 1/2016 | Berg |
| 9,278,916 B2 | 3/2016 | Berg et al. |
| 9,359,288 B2 | 6/2016 | Svadberg et al. |
| 2009/0198085 A1 | 8/2009 | Hayashi et al. |
| 2010/0016626 A1 | 1/2010 | Toyama et al. |
| 2013/0324715 A1 | 12/2013 | Wickstrom et al. |

FOREIGN PATENT DOCUMENTS

| EP | 2017258 A1 | 1/2009 |
|---|---|---|
| EP | 2128130 A1 | 12/2009 |
| EP | 2017258 B1 | 3/2012 |
| EP | 0862464 B1 | 8/2012 |
| EP | 2119458 B1 | 5/2013 |
| EP | 2646411 A1 | 10/2013 |
| EP | 2655320 A1 | 10/2013 |

(Continued)

OTHER PUBLICATIONS

Office Action received for Russian Patent Application No. 2015-101998, dated Jun. 27, 2017, 11 pages. (5 pages English Translation +6 pages Official Copy).
Airbirhio et al. "Efficient Regioselective Labelling of the CFC alternative 1,1,1,2-Tetrafluoroethane (HFC-134a) with fluorine-18", Journal of Fluorine Chemistry, vol. 70, Issue No. 2, 1995, pp. 279-287.
Satyamurty et al. "Electronic Generators for the Production of Positron-Emitter Labeled Radiopharmaceuticals: Where Would PET Be without Them?", Clinical Positron Imaging, vol. 2, Issue No. 5, 1999, pp. 233-253.
McConathy et al. "Improved Synthesis of Anti-[18F]FACBC: Improved Preparation of Labeling Precursor and Automated Radiosynthesis", Applied Radiation and Isotopes, vol. 58, Issue No. 6, 2003, pp. 657-666.

(Continued)

Primary Examiner — Natasha Young
(74) Attorney, Agent, or Firm — Wood IP LLC

(57) ABSTRACT

The present invention provides a method for the production of [$^{18}$F]-FACBC which has advantages over know such methods. Also provided by the present invention is a system to carry out the method of the invention and a cassette suitable for carrying out the method of the invention on an automated radiosynthesis apparatus.

17 Claims, No Drawings

(56) References Cited

FOREIGN PATENT DOCUMENTS

| | | |
|---|---|---|
| EP | 2885271 A1 | 6/2015 |
| EP | 2509637 B1 | 8/2016 |
| EP | 2230229 B1 | 10/2016 |
| EP | 2655321 B1 | 2/2017 |
| EP | 2658831 B1 | 2/2017 |
| JP | 2000-500442 A | 1/2000 |
| JP | 4550141 B2 | 9/2010 |
| JP | 5258583 B2 | 8/2013 |
| JP | 2014-509303 A | 4/2014 |
| JP | 5518337 B2 | 6/2014 |
| JP | 5732198 B2 | 6/2015 |
| JP | 6018578 B2 | 11/2016 |
| JP | 6018581 B2 | 11/2016 |
| JP | 6047100 B2 | 12/2016 |
| RU | 2008148851 A | 6/2010 |
| WO | 1997/017092 A1 | 5/1997 |
| WO | 2007/132689 A1 | 11/2007 |
| WO | 2008/078589 A1 | 7/2008 |
| WO | 2008/099800 A1 | 8/2008 |
| WO | 2009/078396 A1 | 6/2009 |
| WO | 2011/044410 A2 | 4/2011 |
| WO | 2012/072567 A1 | 6/2012 |
| WO | 2012/084794 A1 | 6/2012 |
| WO | 2012/084831 A1 | 6/2012 |
| WO | 2012/089594 A1 | 7/2012 |
| WO | 2012089594 A1 | 7/2012 |
| WO | 2014/023775 A1 | 2/2014 |

OTHER PUBLICATIONS

Wuts et al. "Protective Groups in Organic Synthesis", In Book: Greene's Protective Groups in Organic Synthesis, Fourth Edition, 2007.

GB Search Report dated Nov. 19, 2012 which was issued in connection with GB Patent Application No. 1214220.4 which was filed on Aug. 9, 2012.

Non-Final Office Action received for U.S. Appl. No. 14/420,493, dated Jul. 23, 2015, 9 pages.

Final Office Action received for U.S. Appl. No. 14/420,493, dated Nov. 3, 2010, 7 pages.

Office Action issued in CN Application No. 20138004183839, filed Aug. 3, 2013 (dated Dec. 3, 3015).

Office Action received for Japanese Patent Application No. 2015-525884, dated Mar. 14, 2017, 6 pages. (2 pages English Copy +4 pages Official Copy).

International Search Report and Written Opinion received for PCT Patent Application No. PCT/EP2013/066570, dated Sep. 26, 2013, 7 pages.

International Preliminary Report on Patentability received for PCT Patent Application No. PCT/EP2013/066570, dated Feb. 10, 2015, 5 pages.

GB Search Report dated Nov. 19, 2012 which was issued in connection with GB Patent Application No. 12/14220.4 which was filed on Aug. 9, 2012.

International Search Report and Written Opinion dated Sep. 26, 2013 which was issued in connection with PCT Patent Application No. EP2013/066570 which was filed on Aug. 7, 2013.

Office Action issued in CN Application No. 20138004183839, filed Aug. 3, 2013 (dated Dec. 3, 2015).

PREPARATION OF 18F-FLUCICLOVINE

CROSS-REFERENCE TO RELATED APPLICATIONS

This application is a divisional of U.S. patent application Ser. No. 14/420,493, now U.S. Pat. No. 9,659,288, filed Feb. 9, 2015, which is a filing under 35 U.S.C. §371 of international application number PCT/EP2013/066570, now WO 2014/023775, filed Aug. 7, 2013, which claims priority to application number 1214220.4, filed Aug. 9, 2012 in Great Britain, the entire contents of which are hereby incorporated herein by reference.

TECHNICAL FIELD OF THE INVENTION

The invention relates to a method for the preparation of a radiopharmaceutical compound, in particular an amino acid derivative useful as a positron emission tomography (PET) tracer. The method of the invention is especially suitable when automated and offers advantages over known methods. Particularly, the invention relates to a method for preparation of [$^{18}$F]-1-amino-3-fluorocyclobutane-1-carboxylic acid ([$^{18}$F]-FACBC, also known as [$^{18}$F]-Fluciclovine).

DESCRIPTION OF RELATED ART

The non-natural amino acid [$^{18}$F]-1-amino-3-fluorocyclobutane-1-carboxylic acid ([$^{18}$F]-FACBC, also known as [$^{18}$F]-Fluciclovine) is taken up specifically by amino acid transporters and has shown promise for tumour imaging with positron emission tomography (PET).

A known synthesis of [$^{18}$F]-FACBC begins with the provision of the protected precursor compound 1-(N-(t-butoxycarbonyeamino)-3-[((trifluoromethyl)sulfonyl)oxy]-cyclobutane-1-carboxylic acid ethyl ester. This precursor compound is first labelled with [$^{18}$F]-fluoride:

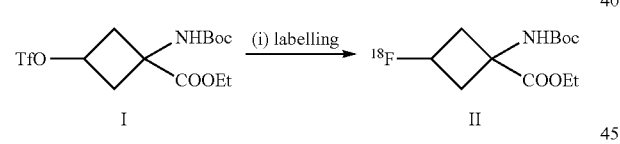

before removal of the two protecting groups:

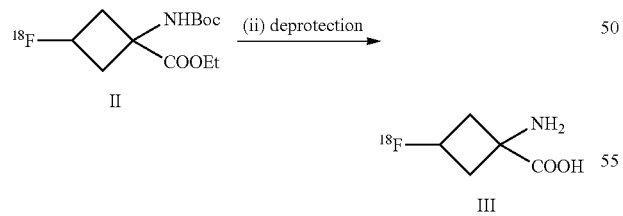

EP2017258 (A1) teaches removal of the ethyl protecting group by trapping the [$^{18}$F]-labelled precursor compound (II) onto a solid phase extraction (SPE) cartridge and incubating with 0.8 mL of a 4 mol/L solution of sodium hydroxide (NaOH). After 3 minutes incubation the NaOH solution was collected in a vial and a further 0.8 mL 4 mol/L NaOH added to the SPE cartridge to repeat the procedure. Thereafter the SPE cartridge was washed with 3 mL water and the wash solution combined with the collected NaOH solution. Then 2.2 mL of 6 mol/L HCl was then added with heating to 60° C. for 5 minutes to remove the Boc protecting group. The resulting solution was purified by passing through (i) an ion retardation column to remove Na$^+$ from excess NaOH and from extra HCl needed to neutralise excess of NaOH to get a highly acidic solution before the acidic hydrolysis step, (ii) an alumina column, and (iii) a reverse-phase column. There is scope for the deprotection step(s) and/or the purification step in the production of [$^{18}$F]-FACBC to be simplified.

SUMMARY OF THE INVENTION

The present invention provides a method for the production of [$^{18}$F]-FACBC which has advantages over know such methods. The method of the present invention is particularly amenable to automation as it permits a simplified purification procedure compared with known methods. In the method of the present invention an extra high volume of H$^+$ is not required in the Boc deprotection step as it is in the prior art Furthermore, an ion removal step such as by means of an ion retardation column such is required in the prior art method is not required by the method of the invention because there is no longer a need for excess ions to be removed. Also provided by the present invention is a system to carry out the method of the invention and a cassette suitable for carrying out the method of the invention on an automated radiosynthesis apparatus.

DETAILED DESCRIPTION OF THE INVENTION

In one aspect the present invention provides a method to prepare 1-amino-3-[$^{18}$F]-fluorocyclobutanecarboxylic acid ([$^{18}$F]-FACBC) wherein said method comprises:
(a) providing a compound of Formula II adsorbed to a solid phase:

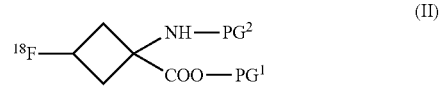

wherein:
PG$^1$ is a carboxy protecting group; and,
PG$^2$ is an amine protecting group;
(b) reacting said adsorbed compound of Formula II with a PG$^1$ deprotecting agent;
(c) sending the PG$^1$ deprotecting agent to waste following said reacting step (b);
(d) passing an elution solution through said solid phase to obtain an eluted compound of Formula III:

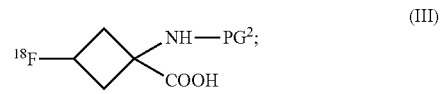

(e) reacting said eluted compound of Formula III obtained in step (d) with a PG$^2$ deprotecting agent to obtain a reaction mixture comprising [$^{18}$F]-FACBC.

The "solid phase" used in step (a) of the method of the invention is contained within a solid phase extraction (SPE) column. Suitably, said solid phase is one having a hydrophobic functional group such as phenyl, cyclohexyl and alkyl, for example one having a structure comprising a support to which $C_{2-18}$ alkyl groups are attached via silicon. In a preferred embodiment, the SPE column is filled with a solid phase having octadecylsilyl groups as functional groups. Moreover, it is preferable to use a column packing having a structure in which the functional groups are not easily detached from the solid phase under aqueous reaction conditions and/or during a long deesterification reaction. In one embodiment the SPE column is a tC18 column.

The compound of Formula II is relatively hydrophobic and therefore has a strong affinity for the solid phase and therefore binds to, or becomes "adsorbed", to said solid phase by virtue of hydrophobic interactions.

The term "protecting group" refers to a group which inhibits or suppresses undesirable chemical reactions, but which is designed to be sufficiently reactive that it may be cleaved from the functional group in question to obtain the desired product under mild enough conditions that do not modify the rest of the molecule. Protecting groups are well known to those skilled in the art and are described in 'Protective Groups in Organic Synthesis', Theorodora W. Greene and Peter G. M. Wuts, (Fourth Edition, John Wiley & Sons, 2007).

The term "reacting" refers to bringing two or more chemical substances (typically referred to in the art as "reactants" or "reagents") together to result in a chemical change in one or both/all of the chemical substances. For example, in the present invention, the step of reacting a $PG^1$ deprotecting agent with an adsorbed compound of Formula II changes said compound of Formula II to a compound of Formula III.

The $PG^1$ "carboxy protecting group" is preferably linear or branched $C_{1-10}$ alkyl chain an aryl substituent. The term "alkyl" used either alone or as part of another group is defined as any straight, branched or cyclic, saturated or unsaturated $C_nH_{2n+1}$ group. term "aryl" refers to any $C_{6-14}$ molecular fragment or group which is derived from a monocyclic or polycyclic aromatic hydrocarbon, or a monocyclic or polycyclic heteroaromatic hydrocarbon. In one embodiment of the method of the invention $PG^1$ is selected from methyl, ethyl, t-butyl and phenyl. In another embodiment of the $PG^1$ is methyl or ethyl and in yet another embodiment $PG^1$ is ethyl.

The $PG^2$ "amine protecting group" suitably prevents reaction between $^{18}F$ and the amino group in the process of providing the compound of Formula II. Examples of suitable amine protecting groups include various carbamate substituents, various amide substituents, various imide substituents, and various amine substituents. Preferably, the amine protecting group is selected from the group consisting of linear or branched $C_{2-7}$ alkyloxycarbonyl substituents, linear or branched $C_{3-7}$ alkenyloxycarbonyl substituents, $C_{7-12}$ benzyloxycarbonyl substituents that may have a modifying group, $C_{2-7}$ alkyldithiooxycarbonyl substituents, linear or branched $C_{1-6}$ alkylamide substituents, linear or branched $C_{2-6}$ alkenylamide substituents, $C_{6-11}$ benzamide substituents that may have a modifying group, $C_{4-10}$ cyclic imide substituents, $C_{6-11}$ aromatic imine substituents that may have a substituent, linear or branched $C_{1-6}$ alkylamine substituents, linear or branched $C_{2-6}$ alkenylamine substituents, and $C_{6-11}$ benzylamine substituents that may have a modifying group. In some embodiments of the invention $PG^2$ is selected from t-butoxycarbonyl, allyloxycarbonyl, phthalimide, and N-benzylideneamine. In other embodiments $PG^2$ is selected from t-butoxycarbonyl or phthalimide. In one embodiment of the invention $PG^2$ is t-butoxycarbonyl.

A "$PG^1$ deprotecting agent" is a reagent capable of removing the carboxy protecting group $PG^1$ from the compound of Formula II during the reacting step (b). Suitable carboxy deprotecting agents are well-known to the skilled person (see Greene and supra) and may be either an acid or an alkaline solution. The concentration of the $PG^1$ deprotecting agent is not limited as long as it is sufficient to remove the carboxy protecting group $PG^1$ and does not have an effect on the final purity or is incompatible with any container used. Preferably the $PG^1$ deprotecting agent is an alkaline solution. In certain embodiments the $PG^1$ deprotecting agent is a sodium hydroxide or a potassium hydroxide solution and in a preferred embodiment is a sodium hydroxide solution, for example of 0.5-5.0 M, preferably 0.5-2.0 M. The reacting step is enabled by closing the outlet of the SPE column so that the $PG^1$ deprotecting agent is retained therein for a specified amount of time. The temperature and the duration of this reacting step need to be sufficient to permit removal of the $PG^1$ carboxy deprotecting group. In certain embodiments the reacting step is carried out at room temperature and for a duration of between 1-5 minutes.

The step of "sending the $PG^1$ deprotecting agent to waste" means that once step (b) is complete (i.e. $PG^1$ is removed from the compound of Formula II), the $PG^1$ deprotecting agent is allowed to pass through the SPE column and is routed out of the reaction system so that it is no longer part of the reaction mixture. An additional benefit is that any impurities soluble in the deprotection solution are also routed out of the reaction system. The $PG^1$ deprotecting agent is therefore substantially removed from the reaction mixture for subsequent steps (d) and (e). As used herein, the term "substantially" refers to the complete or nearly complete extent or degree of an action, characteristic, property, state, structure, item, or result. For example, an object that is substantially enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. For example in the case of removal of the $PG^1$ deprotecting group, the term "substantially removed" can be taken to mean in the $PG^2$ deprotection step (e) that only sufficient $PG^2$ deprotecting agent is required to remove $PG^2$, i.e. it is not required to add extra ion to counter the level of ion present from the $PG^1$ deprotecting step (b).

The "elution solution" of step (d) is suitably one for which the compound of Formula III has more affinity than it has for the solid phase. Suitably, because said compound of Formula III is relatively hydrophilic compared with said solid phase, said elution solution is a hydrophilic solution. In some embodiments of the invention said elution solution is an aqueous solution and in other embodiments said elution solution is water.

The "$PG^2$ deprotecting agent" is a reagent capable of removing the amine protecting group $PG^2$ from the compound of Formula III during the reacting step (e). Suitable such amine deprotecting agents are well-known to the skilled person (see Greene and Wuts, supra) and may be either an acid or an alkaline solution. The concentration of the $PG^2$ deprotecting agent is not limited as long as it is sufficient to remove the carboxy protecting group $PG^2$. Preferably the $PG^2$ deprotecting agent is an acid solution. A suitable acid preferably includes an acid selected from inorganic acids such as hydrochloric acid, sulfuric acid and nitric acid, and organic acids such as perfluoroalkyl carboxylic acid, e.g. trifluoroacetic acid. In certain embodiments, the PG² deprotecting agent is hydrochloric acid, and in other embodiments when HCl is used as PG² deprotecting agent it is at a concentration of 1.0-4.0M. Reacting step (e) is preferably carried out with heat to allow the removal of PG² reaction to proceed more rapidly. The reaction time depends on the reaction temperature or other conditions. For example, when the reacting step (e) is performed at 60° C., a sufficient reaction time is 5 minutes.

In a preferred aspect, the [$^{18}$F]-FACBC is trans-1-amino-3-[$^{18}$F]-fluorocyclobutanecarboxylic acid (anti-[$^{18}$F]-FACBC):

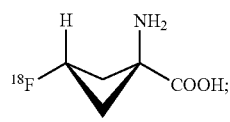

said compound of Formula II is a compound of Formula IIa:

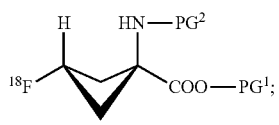

(IIa)

and,
said compound of Formula III is a compound of Formula IIIa:

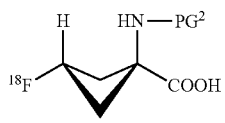

(IIIa)

wherein PG¹ and PG² are as described hereinabove.

Said providing step (a) of the method of the invention may be carried out using methods known in the art, such as for example described by McConathy et al (2003 Appl Radiat Isotop; 58: 657-666).

Suitably, said providing step (a) comprises:
(i) reacting a precursor compound of Formula I:

(I)

with a suitable source of [$^{18}$F]fluoride;
wherein:
LG is a leaving group;
PG¹ is as defined hereinabove; and,
PG² is as defined hereinabove;
to obtain a reaction mixture comprising the compound of Formula II;
(ii) applying the reaction mixture obtained in step (i) to a solid phase so that said compound of Formula II becomes adsorbed to said solid phase, wherein said solid phase is as defined hereinabove.

A "precursor compound" comprises a non-radioactive derivative of a radiolabelled compound, designed so that chemical reaction with a convenient chemical form of the detectable label occurs site-specifically; can be conducted in the minimum number of steps (ideally a single step); and without the need for significant purification (ideally no further purification), to give the desired radiolabelled compound. Such precursor compounds are synthetic and can conveniently be obtained in good chemical purity.

A suitable "leaving group" in the context of the present invention is a chemical group that can be displaced by nucleophilic displacement reaction with fluoride ion. These are well-known in the art of synthetic chemistry. In some embodiments the leaving group of the present invention is a linear or branched $C_{1-10}$ haloalkyl sulfonic acid substituent, a linear or branched $C_{1-10}$ alkyl sulfonic acid substituent, a fluorosulfonic acid substituent, or an aromatic sulfonic acid substituent. In other embodiments of the invention the leaving group is selected from methanesulfonic acid, toluenesulfonic acid, nitrobenzenesulfonic acid, benzenesulfonic acid, trifluoromethanesulfonic acid, fluorosulfonic acid, and perfluoroalkylsulfonic acid. In some embodiments the leaving group is either methanesulfonic acid, trifluoromethanesulfonic acid or toluenesulfonic acid and in another embodiment the leaving group is trifluoromethanesulfonic acid.

In a preferred embodiment, said compound of Formula I is a compound of Formula Ia:

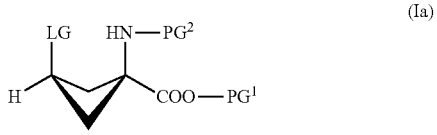

(Ia)

and said compound of Formula II is a compound of Formula IIa:

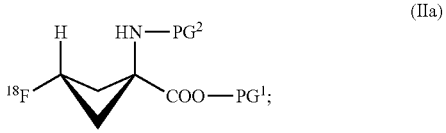

(IIa)

wherein LG, PG¹ and PG² are as previously defined herein.

The "source of [$^{18}$F]fluoride" suitable for use in the invention is normally obtained as an aqueous solution from the nuclear reaction $^{18}O(p,n)^{18}F$. In order to increase the reactivity of fluoride and to reduce or minimise hydroxylated by-products resulting from the presence of water, water is typically removed from [$^{18}$F]-fluoride prior to the reaction, and fluorination reactions are carried out using anhydrous reaction solvents (Aigbirhio et al 1995 J Fluor Chem; 70: 279-87). A further step that is used to improve the reactivity of [$^{18}$F]-fluoride for radiofluorination reactions is to add a cationic counterion prior to the removal of water. Suitably, the counterion should possess sufficient solubility within the anhydrous reaction solvent to maintain the solubility of the [$^{18}$F]-fluoride. Therefore, counterions that are typically used include large but soft metal ions such as rubidium or caesium, potassium complexed with a cryptand such as Kryptofix™, or tetraalkylammonium salts, wherein potassium complexed with a cryptand such as Kryptofix™, or tetraalkylammonium salts are preferred.

In some embodiments the present invention additionally includes the further step (f) of purifying said reaction mixture obtained in step (e) to obtain substantially pure [$^{18}$F]-FACBC.

The term "substantially" as used in "substantially pure" takes the meaning as presented above. The term "substantially pure" as used in the context of [$^{18}$F]-FACBC encompasses completely pure [$^{18}$F]-FACBC or [$^{18}$F]-FACBC that is sufficiently pure to be suitable for use as a PET tracer. The term "suitable for use as a PET tracer" means that the [$^{18}$F]-FACBC product is suitable for intravenous administration to a mammalian subject followed by PET imaging to obtain one or more clinically-useful images of the location and/or distribution of [$^{18}$F]-FACBC.

In one embodiment, step (f) comprises:
(i) carrying out a first purification step comprising passing said reaction mixture through a hydrophilic lipophilic balanced (HLB) solid phase; and,
(ii) optionally carrying out a second purification step comprising passing said reaction mixture through an alumina solid phase.

In certain embodiments of the present invention said purifying step (f) can be said to consist essentially of the above-defined steps. In particular, the purifying step (f) as used in the present invention does not require that the reaction mixture is passed through an ion retardation column. This is a notable distinction over the prior art methods where this is a required step in order to remove ions and to neutralise the reaction mixture (e.g. as described by McConathy et al, supra, and in EP 2 017 258 A1). As such, the method of the present invention is simplified over the prior art methods and as such is more suitable for automation. In a preferred embodiment the method of the invention is automated, and in this embodiment suitably carried out on an automated synthesis apparatus.

In another aspect of the invention is provided a system for carrying out the method of the invention wherein said system comprises:
(a) a solid phase as defined herein for the method of the invention;
(b) a source of $PG^1$ deprotecting agent herein for the method of the invention;
(c) a source of elution solution as defined herein for the method of the invention;
(d) a source of $PG^2$ deprotecting agent as defined herein for the method of the invention;
(e) a reaction container; and,
(f) a waste means;
wherein said system further comprises means permitting sequential flow from:
(i) (e) to (a);
(ii) (b) to (a);
(iii) (a) to (f);
(iv) (c) to (e) via (a); and,
(v) (d) to (e).

The "reaction container" is any vessel suitable for carrying out an $^{18}$F labelling reaction.

The term "waste means" refers for example to a dedicated vessel into which is sent any components of the reaction that are no longer required, along with associated tubing and valves permitting the transfer of these components away from the reaction.

In particular, the system of the invention does not comprise an ion retardation column.

In another embodiment, the system of the invention further comprises:
(g) a source of said precursor compound of Formula I as defined herein; and,
(h) a source of [$^{18}$F]fluoride.

In a further embodiment, the system of the present invention may also comprise (i) means for purifying said reaction mixture obtained in step (e) to obtain substantially pure [$^{18}$F]-FACBC. Said means (i) in certain embodiments may comprise a HLB solid phase and an alumina solid phase.

The system of the invention in one embodiment consists essentially of the above-described features.

[$^{18}$F]-radiotracers in particular are now often conveniently prepared on an automated radiosynthesis apparatus. The method of the invention may therefore be carried out using an automated radiosynthesis apparatus. By the term "automated radiosynthesis apparatus" is meant an automated module based on the principle of unit operations as described by Satyamurthy et al (1999 Clin Positr Imag; 2(5): 233-253). The term "unit operations" means that complex processes are reduced to a series of simple operations or reactions, which can be applied to a range of materials. Suitable automated synthesiser apparatus are commercially available from a range of suppliers including: GE Healthcare Ltd (Chalfont St Giles, UK); CTI Inc. (Knoxville, USA); Ion Beam Applications S.A. (Chemin du Cyclotron 3, B-1348 Louvain-La-Neuve, Belgium); Raytest (Straubenhardt, Germany) and Bioscan (Washington D.C., USA).

Commercial automated radiosynthesis apparatus also provide suitable containers for the liquid radioactive waste generated as a result of the radiopharmaceutical preparation. Automated radiosynthesis apparatus are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours.

Preferred automated radiosynthesis apparatus of the present invention are those which comprise a disposable or single use cassette which comprises all the reagents, reaction vessels and apparatus necessary to carry out the preparation of a given batch of radiopharmaceutical. By use of such cassettes the automated radiosynthesis apparatus has the flexibility to be capable of making a variety of different radiopharmaceuticals with minimal risk of cross-contamination, by simply changing the cassette. The cassette approach also has the advantages of simplified set-up and hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

In a further aspect the present invention provides a cassette for carrying out the method of the invention on an automated synthesis apparatus wherein said cassette comprises the elements as defined for the system of the invention.

For each aspect of the invention, features having the same name have all the same embodiments as described in relation to other aspects of the invention.

BRIEF DESCRIPTION OF THE EXAMPLES

Example 1 describes the synthesis of [$^{18}$F]FACBC according to the method of the invention.

LIST OF ABBREVIATIONS USED IN THE EXAMPLES

[$^{18}$F]FACBC 1-amino-3-[$^{18}$F]fluorocyclobutane-1-carboxylic acid
K222 Kryptofix 222
MeCN acetonitrile
MeOH methanol
QMA quaternary methyl ammonium
RCY radiochemical yield
SPE solid-phase extraction
TLC thin layer chromatography
UV ultraviolet

EXAMPLES

All reagents and solvents were purchased from Merck and used without further purification. The [$^{18}$F]FACBC precursor; Syn-1-(N-(tert-butoxycarbonyl)amino)-3-[[(trifluoromethyl)sulfonyl]oxy]-cyclobutane-1-carboxylic acid ethyl ester was obtained from GE Healthcare. The Oasis HLB plus cartridge and the Sep-Pak cartridges: QMA light Plus (K$_2$CO$_3$ form), tC18 light, Alumina N light were purchased from Waters (Milford, Mass., USA). A Capintec NaI ion chamber was used for all radioactive measurements (model CRC15R). Radio-thin layer chromatography (radio-TLC) was performed on a Packard instant imager using pre-coated plates of silica gel (Merck 60F$_{254}$).

Example 1: Synthesis of [$^{18}$F]FACBC

No-carrier-added [$^{18}$F]fluoride was produced via the $^{18}$O(p,n)$^{18}$F nuclear reaction on a GE PETtrace 6 cyclotron (Norwegian Cyclotron Centre, Oslo). Irradiations were performed using a dual-beam, 30 µA current on two equal Ag targets with HAVAR foils using 16.5 MeV protons. Each target contained 1.6 ml of ≥96% [$^{18}$O]water (Marshall Isotopes). Subsequent to irradiation and delivery to a hotcell, each target was washed with 1.6 ml of [$^{16}$O]water (Merck, water for GR analysis), giving approximately 2-5 Gbq in 3.2 ml of [$^{16}$O]water.

All radiochemistry was performed on a commercially available GE FASTlab™ with single-use cassettes. Each cassette is built around a one-piece-moulded manifold with 25 three-way stopcocks, all made of polypropylene. Briefly, the cassette includes a 5 ml reactor (cyclic olefin copolymer), one 1 ml syringe and two 5 ml syringes, spikes for connection with five prefilled vials, one water bag (100 ml) as well as various SPE cartridges and filters. Fluid paths are controlled with nitrogen purging, vacuum and the three syringes. The fully automated system is designed for single-step fluorinations with cyclotron-produced [$^{18}$F]fluoride. The FASTlab was programmed by the software package in a step-by-step time-dependent sequence of events such as moving the syringes, nitrogen purging, vacuum, and temperature regulation. Synthesis of [$^{18}$F]FACBC followed the three general steps: (a) [$^{18}$F]fluorination, (b) hydrolysis of protection groups and (c) SPE purification.

Vial A contained K$_{222}$ (58.8 mg, 156 µmol), K$_2$CO$_3$ (8.1 mg, 60.8 µmol) in 79.5% (v/v) MeCN$_{(aq)}$ (1105 µl). Vial B contained 4M HCl (2.0 ml). Vial C contained MeCN (4.1 ml). Vial D contained the precursor (48.4 mg, 123.5 µmol) in its dry form (stored at −20° C. until cassette assembly). Vial E contained 2 M NaOH (4.1 ml). The 30 ml product collection glass vial was filled with 200 mM trisodium citrate (10 ml). Aqueous [$^{18}$F]fluoride (1-1.5 ml, 100-200 Mbq) was passed through the QMA and into the $^{18}$O—H$_2$O recovery vial. The QMA was then flushed with MeCN and sent to waste. The trapped [$^{18}$F]fluoride was eluted into the reactor using eluent from vial A (730 µl) and then concentrated to dryness by azeotropic distillation with acetonitrile (80 vial C). Approximately 1.7 ml of MeCN was mixed with precursor in vial D from which 1.0 ml of the dissolved precursor (corresponds to 28.5 mg, 72.7 mmol precursor) was added to the reactor and heated for 3 min at 85° C. The reaction mixture was diluted with water and sent through the tC18 cartridge. Reactor was washed with water and sent through the tC18 cartridge. The labelled intermediate, fixed on the tC18 cartridge was washed with water, and then incubated with 2M NaOH (2.0 ml) for 5 min after which the 2M NaOH was sent to waste. The labelled intermediate (without the ester group) was then eluted off the tC18 cartridge into the reactor using water. The BOC group was hydrolysed by adding 4M HCl (1.4 ml) and heating the reactor for 5 min at 60° C. The reactor content with the crude [$^{18}$F]FACBC was sent through the HLB and Alumina cartridges and into the 30 ml product vial. The HLB and Alumina cartridges were washed with water (9.1 ml total) and collected in the product vial. Finally, 2M NaOH (0.9 ml) and water (2.1 ml) was added to the product vial, giving a purified formulation of [$^{18}$F]FACBC with a total volume of 26 ml. Radiochemical purity was measured by radio-TLC using a mixture of MeCN:MeOH:H$_2$O:CH$_3$COOH (20:5:5:1) as the mobile phase. The radiochemical yield (RCY) was expressed as the amount of radioactivity in the [$^{18}$F]FACBC fraction divided by the total used [$^{18}$F]fluoride activity (decay corrected). Total synthesis time was 43 min.

The RCY of [$^{18}$F]FACBC was 62.5%±1.93 (SD), n=4.

What is claimed is:

1. A system for carrying out a method to prepare 1-amino-3-[$^{18}$F]-fluorocyclobutanecarboxylic acid ([$^{18}$F]-FACBC) comprising:
   (a) a solid phase having compound of Formula II adsorbed on its surface

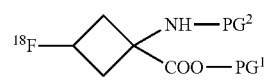

(II)

wherein:
   PG$^1$ is a carboxy protecting group; and,
   PG$^2$ is an amine protecting group;
   (b) a source of PG$^1$ deprotecting agent to be reacted with said compound of Formula II;
   (c) a source of elution solution to be passed through said solid phase to obtain an eluted compound of Formula III:

(III)

(d) a source of PG$^2$ deprotecting agent to be reacted with said compound of Formula III to obtain a reaction mixture comprising [$^{18}$F]-FACBC;

(e) a reaction container; and,
(f) a waste means;
wherein said system further comprises means permitting sequential flow from:
(i) (e) to (a);
(ii) (b) to (a);
(iii) (a) to (f);
(iv) (c) to (e) via (a); and,
(v) (d) to (e).

2. The system as defined in claim 1 wherein said compound of Formula II is a compound of Formula IIa:

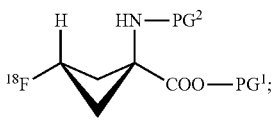

wherein $PG^1$ and $PG^2$ are as defined in claim 1.

3. The system as defined in claim 1 wherein $PG^1$ is ethyl.
4. The system as defined in claim 1 wherein $PG^2$ is t-butoxycarbonyl.
5. The system as defined in claim 1 wherein said solid phase is a tC18 solid phase extraction (SPE) column.
6. The system as defined in claim 1 wherein said $PG^1$ deprotecting agent is NaOH.
7. The system as defined in claim 1 wherein said $PG^2$ deprotecting agent is HCl.
8. The system as defined in claim 1 wherein said elution solution is water.
9. The system as defined in claim 1 further comprising a hydrophilic lipophilic balanced (HLB) solid phase to purify said 1-amino-3-[18F]-fluorocyclobutanecarboxylic acid.
10. The system as defined in claim 9 further comprising a second purification means comprising an alumina solid phase.
11. The system as defined in claim 1 wherein said system is suitable for use with an automated radiosynthesis apparatus.
12. A system for carrying out said method to prepare 1-amino-3-[$^{18}$F]-fluorocyclobutanecarboxylic acid ([$^{18}$F]-FACBC) comprising the system as defined in claim 1 and further comprising:
(g) a source of a precursor compound of Formula I

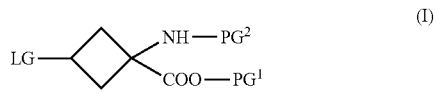

wherein:
LG is a leaving group;
$PG^1$ as defined in claim 1; and,
$PG^2$ is as defined in claim 1; and,
(h) a source of [$^{18}$F]fluoride.

13. The system as defined in claim 12 wherein said compound of Formula I is a compound of Formula Ia:

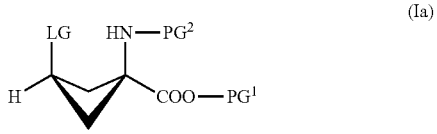

wherein LG is as defined in claim 12, $PG^1$ is as defined in claim 1, and $PG^2$ is as defined in claim 1.

14. The system as defined in claim 12 wherein LG is trifluoromethanesulfonate.
15. A cassette comprising the system as defined in claim 9 for use on an automated synthesis apparatus.
16. A cassette comprising the system as defined in claim 1 for use on an automated synthesis apparatus.
17. A cassette comprising the system as defined in claim 10 for use on an automated synthesis apparatus.

* * * * *